(12) United States Patent  
Butera et al.

(10) Patent No.: US 11,839,478 B2  
(45) Date of Patent: *Dec. 12, 2023

(54) NEURAL INTERFACING DEVICE

(71) Applicants: BIOCIRCUIT TECHNOLOGIES, INC., Atlanta, GA (US); GEORGIA TECH RESEARCH CORPORATION, Atlanta, GA (US)

(72) Inventors: Robert J. Butera, Decatur, GA (US); Yogi A. Patel, Marietta, GA (US); James D. Ross, Decatur, GA (US); Swaminathan Rajaraman, Decatur, GA (US); Isaac Clements, Marietta, GA (US)

(73) Assignee: BioCircuit Technologies, Inc. Georgia Tech Research Corporation, Atlanta, GA (US)

( * ) Notice: Subject to any disclaimer, the term of this patent is extended or adjusted under 35 U.S.C. 154(b) by 185 days.

This patent is subject to a terminal disclaimer.

(21) Appl. No.: 17/215,193

(22) Filed: Mar. 29, 2021

(65) Prior Publication Data

US 2021/0236033 A1 Aug. 5, 2021

Related U.S. Application Data

(63) Continuation of application No. 15/115,772, filed as application No. PCT/US2015/014122 on Feb. 2, 2015, now Pat. No. 10,959,631.

(Continued)

(51) Int. Cl.
*A61B 5/294* (2021.01)
*A61B 5/00* (2006.01)
(Continued)

(52) U.S. Cl.
CPC ............ *A61B 5/294* (2021.01); *A61B 5/4041* (2013.01); *A61B 5/685* (2013.01); *A61B 5/6877* (2013.01);
(Continued)

(58) Field of Classification Search
CPC ......... A61B 5/24; A61B 5/259; A61B 5/6877; A61B 5/294; A61N 1/0551; A61N 1/0553; A61N 1/0556
See application file for complete search history.

(56) References Cited

U.S. PATENT DOCUMENTS

| 4,461,304 A | 7/1984 | Kuperstein |
| 5,215,088 A | 6/1993 | Normann et al. |

(Continued)

OTHER PUBLICATIONS

Ackermann, Jr., D.M., et al., "Effect of Nerve Cuff Electrode Geometry on Onset Response Firing in High-Frequency Nerve Conduction Block," IEEE Transactions on Neural Systems and Rehabilitation Engineering, vol. 18, No. 6, 2010, pp. 658-665.

(Continued)

*Primary Examiner* — Eun Hwa Kim
(74) *Attorney, Agent, or Firm* — Meunier Carlin & Curfman LLC

(57) ABSTRACT

A neural interfacing device is disclosed. The neural interfacing device includes a microneedle electrode. The microneedle electrode includes a body having a void formed therein and a plurality of microneedles. The void surrounds the plurality of microneedles, and the plurality of microneedles are bent outward with respect to the body to form a three-dimensional microneedle electrode. Additionally, each of the plurality of microneedles is sized and shaped to penetrate a nerve epineurium.

19 Claims, 9 Drawing Sheets

Related U.S. Application Data

(60) Provisional application No. 61/934,708, filed on Feb. 1, 2014.

(51) Int. Cl.
  *A61N 1/05* (2006.01)
  *A61N 1/36* (2006.01)

(52) U.S. Cl.
  CPC ......... *A61N 1/0551* (2013.01); *A61N 1/0556* (2013.01); *A61N 1/3605* (2013.01); *A61B 2562/0209* (2013.01); *A61B 2562/046* (2013.01)

(56) References Cited

U.S. PATENT DOCUMENTS

| | | | |
|---|---|---|---|
| 5,400,784 | A | 3/1995 | Durand |
| 8,359,083 | B2 | 1/2013 | Clark et al. |
| 8,588,884 | B2 | 11/2013 | Hegde et al. |
| 9,700,221 | B2 | 7/2017 | Rajaraman et al. |
| 2004/0006264 | A1 | 1/2004 | Mojarradi |
| 2007/0118070 | A1* | 5/2007 | Cormier ............. A61B 5/15105 604/21 |
| 2007/0191910 | A1 | 8/2007 | Ren |
| 2007/0213629 | A1 | 9/2007 | Greene |
| 2008/0138581 | A1 | 6/2008 | Bhandari et al. |
| 2008/0138583 | A1 | 6/2008 | Bhandari et al. |
| 2009/0192571 | A1 | 7/2009 | Stett et al. |
| 2011/0144467 | A1 | 6/2011 | Yao et al. |
| 2013/0253299 | A1 | 9/2013 | Weber et al. |

OTHER PUBLICATIONS

Boger, A., et al., "Different clinical electrodes achieve similar electrical nerve conduction block," Journal of Neural Engineering, vol. 10, 2013, 9 pages.
Branner, A., et al., "A multielectrode array for intrafascicular recording and stimulation in sciatic nerve of cats," Brain Research Bulletin, vol. 51, No. 4, 2000, pp. 293-306.
Branner, A., et al., "Long-Term Stimulation and Recording With a Penetrating Microelectrode Array in Cat Sciatic Nerve," IEEE Transactions on Biomedical Engineering, vol. 51, No. 1, 2004, pp. 146-157.
Branner, A., et al., "Selective Stimulation of Cat Sciatic Nerve Using an Array of Varying-Length Microelectrodes," Journal of Neuropsychology, vol. 85, No. 4, 2001, pp. 1585-1594.
Fitzpatrick, D.M., et al., "A Nerve Cuff Design for the Selective Activation and Blocking of Myelinated Nerve Fibres," Neuromuscular Systems, Annual International Conference of the IEEE Engineering in Medicine and Biology Society, vol. 13, No. 2, 1991, pp. 906-907.
Harreby, K.R., et al., "Subchronic Stimulation Performance of Transverse Intrafascicular Multichannel Electrodes in the Median Nerve of the Göttingen Minipig," Artificial Organs, vol. 39, No. 2, Feb. 2015, pp. E36-E48.
Jellema, T., et al., "A Miniaturized Cuff Electrode for Electrical Stimulation of Peripheral Nerves in the Freely Moving Rat," Brain Research Bulletin, vol. 37, No. 6, 1995, pp. 551-554.
Korivi, N.S., et al., "Self-closing Cuff Electrode for Functional Neural Stimulation and Recording," Journal of Medical and Biological Engineering, vol. 31, No. 5, 2011, pp. 353-357.
Leventhal, D.K., et al., "Subfascicle Stimulation Selectivity Using a FINE," Proceedings of the $22^{nd}$ Annual EMBS International Conference, 2000, 3 pages.
Loeb, G.E., et al., "Cuff electrodes for chronic stimulation and recording of peripheral nerve activity," Journal of Neuroscience Methods, vol. 64, 1996, pp. 95-103.
Malagodi, M.S., et al., "An Intrafascicular Electrode for Recording of Action Potentials in Peripheral Nerves," Annals of Biomedical Engineering, vol. 17, 1989, pp. 397-410.
Mathews, K.S., et al., "Assessment of Rat Sciatic Nerve Function Following Acute Implantation of High Density Utah Slanted Electrode Array (25 Electrodes/$mm^2$) Based on Neural Recordings and Evoked Muscle Activity," Muscle & Nerve, Sep. 2014, pp. 417-424.
Naples, G.G., et al., "A Spiral Nerve Cuff Electrode for Peripheral Nerve Stimulation," IEEE Transactions on Biomedical Engineering, vol. 35, No. 1, 1988, pp. 905-916.
Navarro, X., et al., "A critical review of interfaces with the peripheral nervous system for the control of neuroprostheses and hybrid bionic systems," Journal of the Peripheral Nervous Systems, vol. 10, 2005, pp. 229-258.
Rousche, P.J., et al., "Chronic recording capability of the Utah Intracortical Electrode Array in cat sensory cortex," Journal of Neuroscience Methods, vol. 82, 1998, pp. 1-15.
Sahin, M., et al., "Improved Nerve Cuff Electrode Recordings with Subthreshold Anodic Currents," IEEE Transactions on Biomedical Engineering, vol. 45, No. 8, 1998, pp. 1044-1050.
Sweeney, J.D., et al., "A Nerve Cuff Technique for Selective Excitation of Peripheral Nerve Trunk Regions," IEEE Transactions on Biomedical Engineering, vol. 37, No. 7, 1990, pp. 706-715.
Taylor, J., et al., "Multiple-electrode nerve cuffs for low-velocity and velocity-selective neural recording," Medical and Biological Engineering Computing, vol. 42, 2004, pp. 634-643.
Tyler, D.J., et al., "A Slowly Penetrating Interfascicular Nerve Electrode for Selective Activation of Peripheral Nerves," IEEE Transactions on Rehabilitation Engineering, vol. 5, No. 1, 1997, pp. 51-61.
Tyler, D.J., et al., "Functionally Selective Peripheral Nerve Stimulation With a Flat Interface Nerve Electrode," IEEE Transactions on Neural Systems and Rehabilitation Engineering, vol. 10, No. 4, 2002, pp. 294-303.
Wang, K., et al., "Flexible Nerve Stimulation Electrode With Iridium Oxide Sputtered on Liquid Crystal Polymer," IEEE Transactions on Biomedical Engineering, vol. 56, No. 1, 2009, pp. 6-14.
Yoshida, K., et al., "Selective Stimulation of Peripheral Nerve Fibers using Dual Intrafascicular Electrodes," IEEE Transactions on Biomedical Engineering, vol. 40, No. 5, 1993, pp. 492-494.
Yu, H., et al., "A Parylene Self-Locking Cuff Electrode for Peripheral Nerve Stimulation and Recording," Journal of Microelectromechanical Systems, vol. 23, No. 5, Oct. 2014, pp. 1025-1035.
International Preliminary Report on Patentability and Written Opinion, dated Aug. 2, 2016, received in connection with International Patent Application No. PCT/US2015/014122.

* cited by examiner

NEURAL INTERFACING DEVICE

This application is a continuation of U.S. patent application Ser. No. 15/115,772, filed on Aug. 1, 2016, which is a national stage application filed under 35 U.S.C. § 371 of PCT/US2015/014122, filed on Feb. 2, 2015, which claims priority to U.S. Provisional Patent Application No. 61/934,708, filed on Feb. 1, 2014, the disclosures of which are hereby incorporated by reference in their entireties.

BACKGROUND OF THE INVENTION

Implementations described herein relate generally to neural interfacing devices configured to electrically stimulate and/or record electrical activity of nerves.

Electrical stimulation can be employed for stimulating, inhibiting, or otherwise manipulating nerves, including peripheral nerves, cranial nerves, optic nerves, spinal nerves, autonomic nerves, nerve ganglia, plexuses of nerves, nervous tissue, and the like. The effects of electrical stimulation on a nerve and characteristics of neural recordings can be at least partially controlled by the characteristics of the electrode used to contact the nerve. A major challenge in the art is minimizing the electrical current or voltage delivered by the electrode required to achieve the desired effect on the target nerve.

Existing approaches for interfacing nerves include interfaces that are affixed external to various tissue layers that typically surround nerves. Electrodes in these configurations are separated from target axons by one or more layers of tissue such as epineural tissue, connective tissues, fatty tissues, etc. that can be of high electrical impedance. In a stimulation setting, these tissues can require that more charge be delivered from the stimulating electrode to achieve the desired effect on target axons and in a recording setting obscure signals from target axons. Extraneural interfaces can also face challenges of migrating in space over time with respect to target axons.

Previous studies have shown that selective stimulation and/or recording capabilities are enhanced in interfascilar or intraneural interfaces, but these approaches are significantly invasive to the nerve. Additionally, their long-term efficacy and safety depend heavily upon the surgical technique used to implant them, and the electrodes are prone to damage from motion.

Accordingly, a need exists for improved neural interface and systems and methods thereof that are minimally invasive, reduce the required charge to be delivered to a nerve, increase the fidelity of recorded nerve activity, and provide stability to maintain the electrode position on the nerve.

SUMMARY

It is to be understood that this summary is not an extensive overview of the disclosure. This summary is exemplary and not restrictive, and it is intended to neither identify key or critical elements of the disclosure nor delineate the scope thereof. The sole purpose of this summary is to explain and exemplify certain concepts of the disclosure as an introduction to the following complete and extensive detailed description.

In one embodiment, the present disclosure provides for a neural interfacing device comprising a microneedle electrode. The microneedle electrode may have one or more microneedles. The one or more microneedles may be shaped and positioned such that when the neural interfacing device is applied to a nerve, the microneedle penetrates a nerve epineurium without any portion of the microneedle electrode penetrating any nerve axon beyond a depth of 500 micrometers.

In another aspect, the neural interfacing device can be configured in a bipolar assembly having two microneedle electrodes. In another aspect, the neural interfacing device can be configured in a tri-polar assembly having three microneedle electrodes. In a further aspect, the neural interfacing device can be configured in a multi-channel array that is selectively configurable via external electronics in electrical communication with the plurality of microneedle electrodes.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

DETAILED DESCRIPTION

Figure 1:
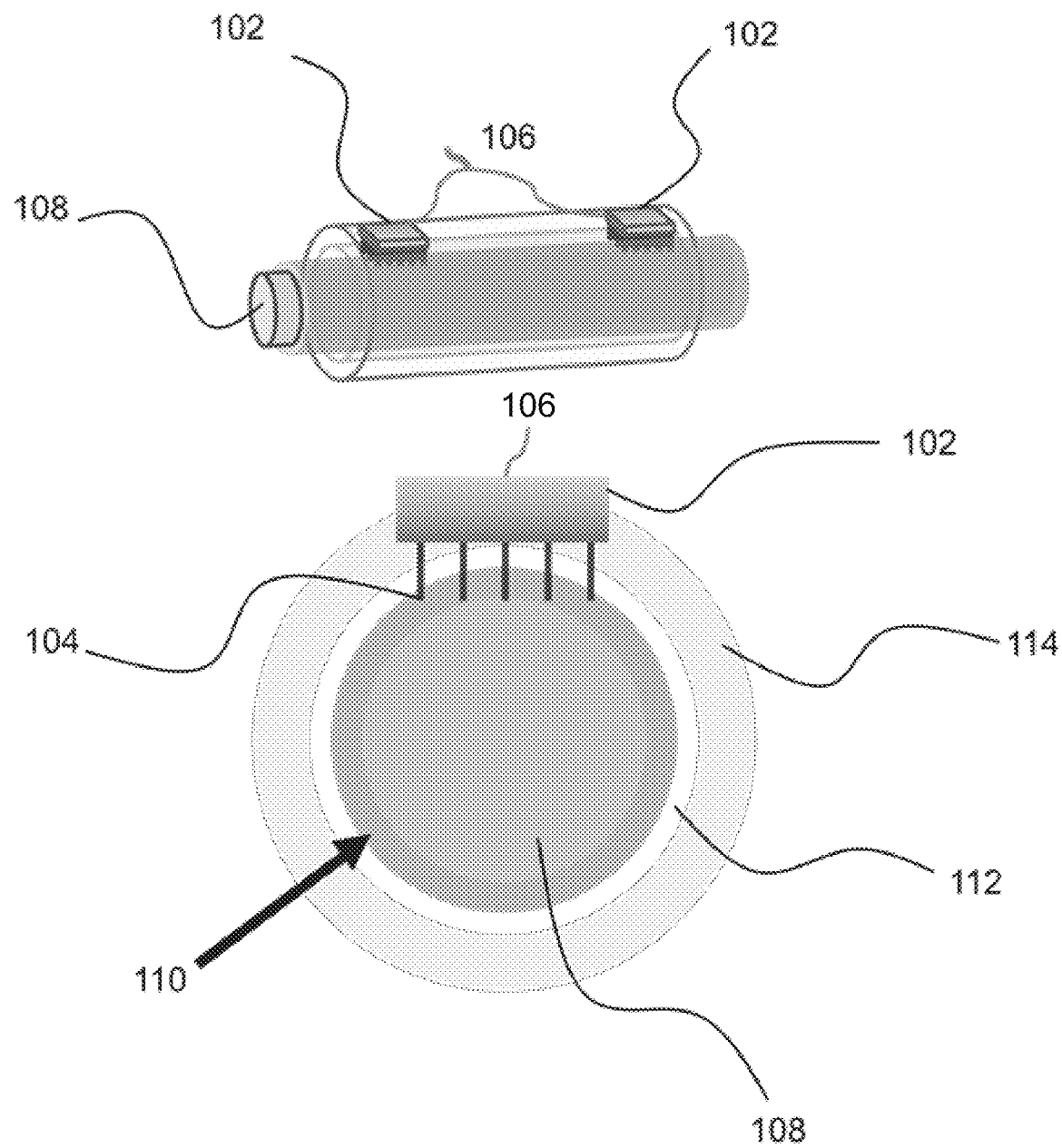
FIG. 1 is a perspective view and cross-sectional view of a schematic showing a neural interfacing device interfacing with a nerve.

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. To this end, those skilled in the relevant art will recognize and appreciate that many changes can be made to the various aspects of the invention described herein, while still obtaining the beneficial results described herein. It will also be apparent that some of the desired benefits described herein can be obtained by selecting some of the features described herein without utilizing other features. Accordingly, those who work in the art will recognize that many modifications and adaptations to the present invention are possible and can even be desirable in certain circumstances and are a part described herein. Thus, the following description is provided as illustrative of the principles described herein and not in limitation thereof.

Reference will be made to the drawings to describe various aspects of one or more implementations of the invention. It is to be understood that the drawings are diagrammatic and schematic representations of one or more implementations, and are not limiting of the present disclosure. Moreover, while various drawings are provided at a scale that is considered functional for one or more implementations, the drawings are not necessarily drawn to scale for all contemplated implementations. The drawings thus represent an exemplary scale, but no inference should be drawn from the drawings as to any required scale.

In the following description, numerous specific details are set forth in order to provide a thorough understanding described herein. It will be obvious, however, to one skilled in the art that the present disclosure may be practiced without these specific details. In other instances, well known aspects of electrical nerve stimulation and microfabrication techniques have not been described in particular detail in order to avoid unnecessarily obscuring aspects of the disclosed implementations.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be predefined it is understood that each of these additional steps can be predefined with any specific aspect or combination of aspects of the disclosed methods.

Implementations described herein are directed toward devices, systems and methods for neural interfacing, for example and without limitation, neural interfacing devices having microneedle electrodes. In one or more aspects, the neural interfacing device described herein comprises an elongate cuff body having a right and a left distal portion that communicate to define a lumen having a substantially reclosable opening. At least one microneedle electrode is fixed on an interior surface of the lumen defined by the cuff body. The at least one microneedle electrode comprises an array of microneedles. In one implementation, the neural interfacing device comprises at least one microneedle electrode having surface functionalized with microneedles that maximizes stimulation or inhibition of activity in but minimizes the charge delivered to the target nerve.

Reference will now be made to the drawings to describe various aspects of one or more implementations of the invention. It is to be understood that the drawings are diagrammatic and schematic representations of one or more implementations, and are not limiting of the present disclosure. Moreover, while various drawings are provided at a scale that is considered functional for one or more implementations, the drawings are not necessarily drawn to scale for all contemplated implementations. The drawings thus represent an exemplary scale, but no inference should be drawn from the drawings as to any required scale.

In the following description, numerous specific details are set forth in order to provide a thorough understanding described herein. It will be obvious, however, to one skilled in the art that the present disclosure may be practiced without these specific details. In other instances, well-known aspects of electrical nerve stimulation and microfabrication techniques have not been described in particular detail in order to avoid unnecessarily obscuring aspects of the disclosed implementations.

FIG. 1 shows two views of an example embodiment of a neural interfacing device interfacing with a nerve. In this particular embodiment, the neural interfacing device has two microneedle electrodes 102. However, in other embodiments the neural interfacing device may have one microneedle electrode 102. In yet other embodiments, the neural interfacing device may have up to 100 microneedle electrodes 102 or more. Each microneedle electrode 102 may comprise at least one microneedle 104. In the embodiment of FIG. 1, each microneedle electrode 102 comprises an array of microneedles 104. In other embodiments, each microneedle electrode 102 may have between 1 up to about 1000 microneedles 104 or more. The microneedles 104 may be arranged in any pattern, including for example a three-dimensional array, grid pattern, or different pattern.

Microneedle electrodes 102 may be connected to one another and/or connected to other electronic devices via electrical connectors 106. Electrical connectors 106 may include any means for transmitting electrical charge and/or data. For example, the electrical connectors 106 may comprise wires, PCB boards, and/or flexible PCB with stretchable traces. In other embodiments, some of the electrical connectors 106 may be omitted in favor of a wireless transmitting device.

In some embodiments, the neural interfacing device comprises a body portion upon which one or more microneedle electrodes 102 may be mounted. For example, the embodiment of FIG. 1 shows an elongate cuff 114 upon which the microneedle electrodes 102 are mounted. However, the present disclosure is not limited to the use of an elongate cuff. In other embodiments, the microneedle electrodes 102 are mounted to a surface of a planar base. In some embodiments, the type of nerve can influence the preferred body portion for mounting a microneedle electrode. For example, for stimulating a standalone nerve that has adequate access, an elongate cuff may be used to at least partially surround a portion of the nerve. On the other hand, stimulating a tightly packed bundle of nerves may be more efficiently accomplished using a planar base that contacts the bundle of nerves rather than surrounding the nerves. In other embodiments, either a planar base or an elongate cuff, or both, may be employed. In other embodiments the planar base and the microneedle may be formed monolithically utilizing a biocompatible polymer that can be metallized to define microneedle electrodes. Other types of body portions may be used to mount the microneedle electrodes as well.

In some embodiments, the neural interfacing device comprises an elongate cuff body having a right and a left distal portion that communicate to define a lumen having a substantially re-closable opening. The cuff body need not completely enclose a nerve. For example, it may only enclose a portion of the nerve while leaving a portion of the nerve undisturbed. In that sense the word "lumen" is not intended to necessarily require a fully enclosed cavity or area.

In FIG. 1, an elongate cuff 114 is shown for securing the microneedle electrodes 102 to a nerve. A space 112 is shown in between the elongate cuff 114 and the nerve. However, the space 112 need not be maintained. In practice there may be more or less space, or none at all.

In the embodiment of FIG. 1, the microneedles 104 penetrate the epineurium 110 layer of the nerve. A person of ordinary skill in the art would recognize that the microneedles 104 may also penetrate other tissue layers, such as connective tissue, peripheral tissue, and others, while also penetrating the epineurium 110. Additionally, not all of the microneedles 104 must penetrate the epineurium 110. In some embodiments, only one microneedle 104 can penetrate the epineurium 110. When multiple microneedles 104 are employed, different microneedles 104 may penetrate to different depths with the epineurium 110 and may penetrate all the way through the epineurium 110.

FIG. 1 illustrates a general axon area 108 in the center of the nerve. A person of ordinary skill in the art would recognize that nerves typically contain many axons. For ease of discussion, these many axons are described as the "axon area," "axons," or "axon," interchangeably. In the embodiment of FIG. 1, none of the microneedles 104 penetrate into the axon area 108. In other embodiments, at least one microneedle 104 may penetrate the axon area 108 up to a depth that constitutes minimal invasion into the axons. For example, in some embodiments the microneedles 104 do not penetrate more than about 500 micrometers into the axon area 108 or, alternatively stated, do not penetrate more than about 500 micrometers into any particular axon of the nerve at issue. In other embodiments, the microneedles 104 do not penetrate more than about 400 micrometers. In another embodiment, the microneedles 104 do not penetrate more than about 300 micrometers. In a further embodiment, the microneedles 104 do not penetrate more than about 200 micrometers. In yet another embodiment, the microneedles 104 do not penetrate more than about 100 micrometers. Finally, in some embodiments, the microneedles 104 do not penetrate the axon area 108, and/or any particular axon, at all.

Figure 2:
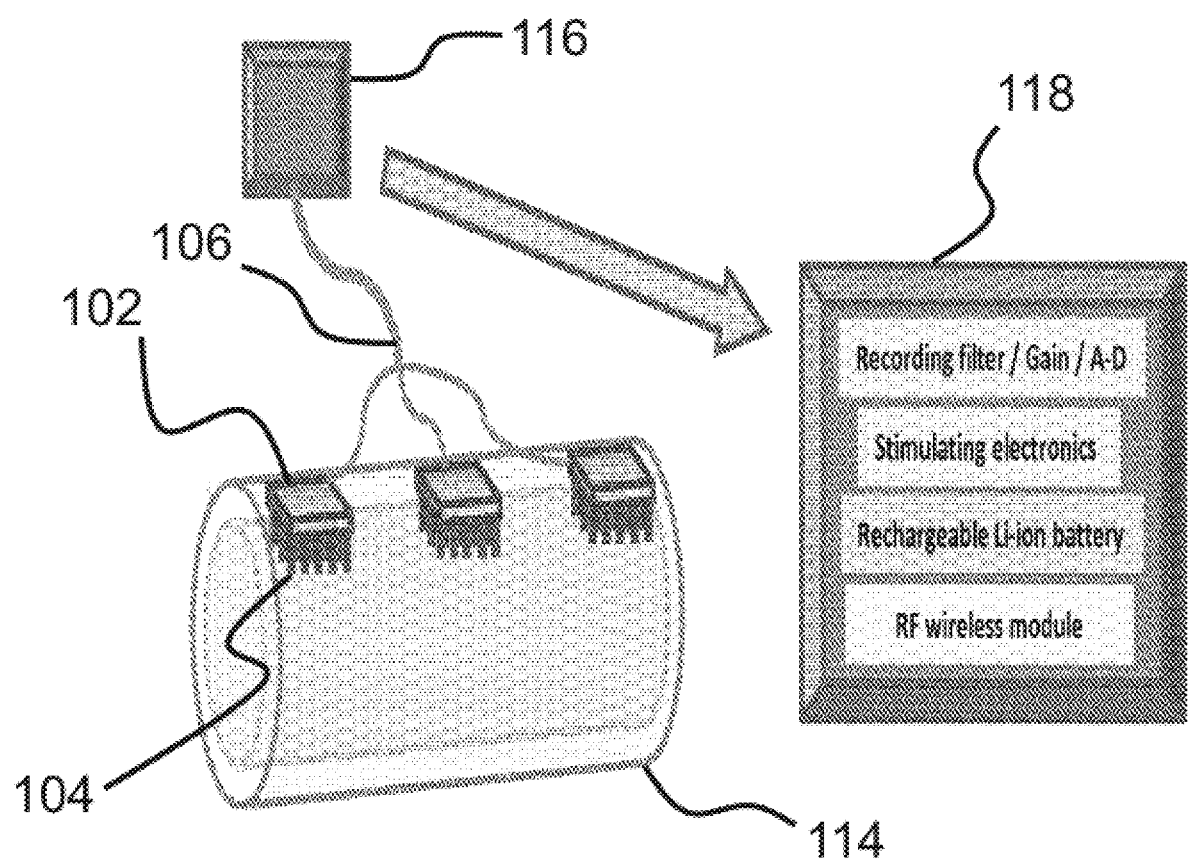
FIG. 2 is a perspective view of a schematic showing a neural interfacing device having three microneedle electrodes connected to stimulating electronics.

FIG. 2 shows an embodiment of a neural interfacing device having three microneedle electrodes 102. Each microneedle electrode 102 is connected to at least one electronics module 116. The connection may be made via electrical connectors 106. An expanded view of the electronics module 116 is shown in FIG. 2 and labeled as 118. The expanded view provides a few examples of what the electronics module 116 may include. For example, it may include stimulating electronics for stimulating nerves, recording electronics including filters, amplifiers, and/or analog-digital converter. It may also include a rechargeable battery. A wireless transmitter may also be included in order to transmit information to, for example, a computer or other electronic device. In some embodiments, the electronics module 116 itself may be a computer, smartphone, tablet, or other computing device.

The embodiment of FIG. 2 shows three microneedle electrodes 102. As explained above, the neural interfacing device may comprise any number of microneedle electrodes 102. In some embodiments, where more than one microneedle electrode 102 is used, at least one of the microneedle electrodes 102 is a stimulating electrode that provides an electrical stimulus to a nerve, while at least one of the remaining microneedle electrodes 102 is a reference electrode. When more than two microneedle electrodes 102 are used, any combination of stimulating electrodes and reference electrodes may be employed.

In one aspect, the nerve interfacing device can comprise two microneedle electrodes that form a bipolar electrode assembly. Here, the first microneedle electrode can be configured as a stimulation electrode and the second microneedle electrode can be configured as a reference or a ground electrode. In another aspect, the electrode assembly can comprise three electrodes that form a tri-polar electrode assembly. Here, in one aspect, the first and second microneedle electrodes communicate to form a reference electrode and the third electrode is configured as a stimulation electrode. In a further aspect, the microneedle electrodes can be configured in a multichannel array that is selectively configurable via stimulation electronics in electrical communication with the plurality of microneedle electrodes.

Figure 3:
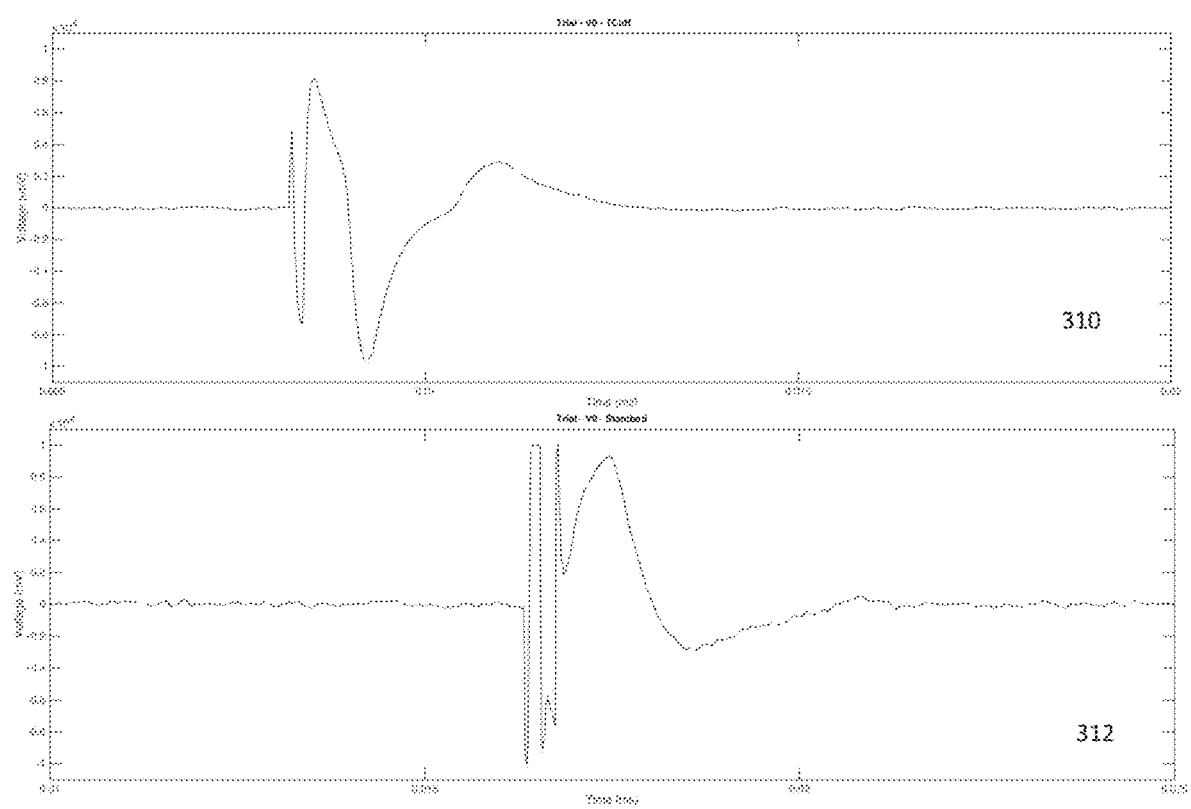
FIG. 3 is a graphical comparison of the noise inherent to electrical stimulation of a nerve using standard electrodes versus microneedle electrodes.

FIG. 3 provides an example graphical comparison of the raw signals obtained from a neural interface device using standard electrodes versus microneedle electrodes. Both graphs show raw data recording during upstream electrical stimulation of a rat sciatic nerve. Graph 312 depicts the recording of compound activity using a tri-polar design with standard "off the shelf" electrodes having no microneedles. Graph 310 depicts recording of the same activity using microneedle electrodes disclosed herein. From left to right, the initial signal deflections represent the electrical stimulation artifact. This artifact is followed by an "A fiber" or "fast component" response shown as the next large signal deflections. Enhanced signal-to-noise ratio is merely one advantage of the disclosed microneedle electrodes herein.

Figure 4:
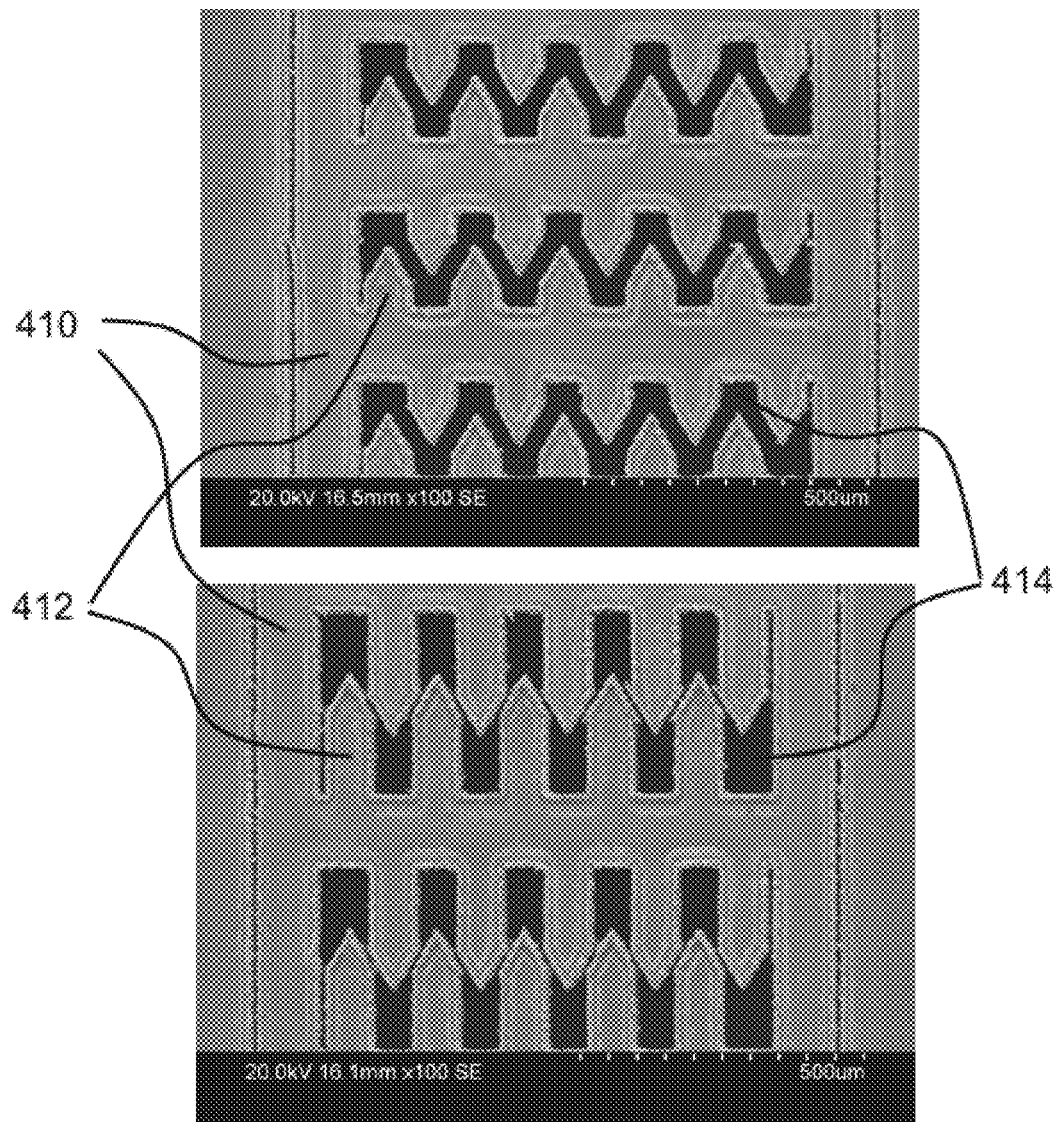
FIG. 4 is a top-down view of microneedle electrodes having different types of microneedles.

FIG. 4 shows a design drawing of two example embodiments of the present disclosure. In these embodiments, microneedle electrodes 410 are shown having an array of microneedles 412. In one embodiment, the microneedles 412 are formed by removing material from portions of the microneedle electrodes 410 to create voids 414. As a result of those voids 414, a force may be applied to fold the microneedles 412 away from the body of the microneedle electrodes 410 such that the microneedles 412 extend outward in a three-dimensional fashion. As illustrated by these two embodiments, the size and shape of the microneedles 412 may vary according to the desired implementation.

Figure 5:
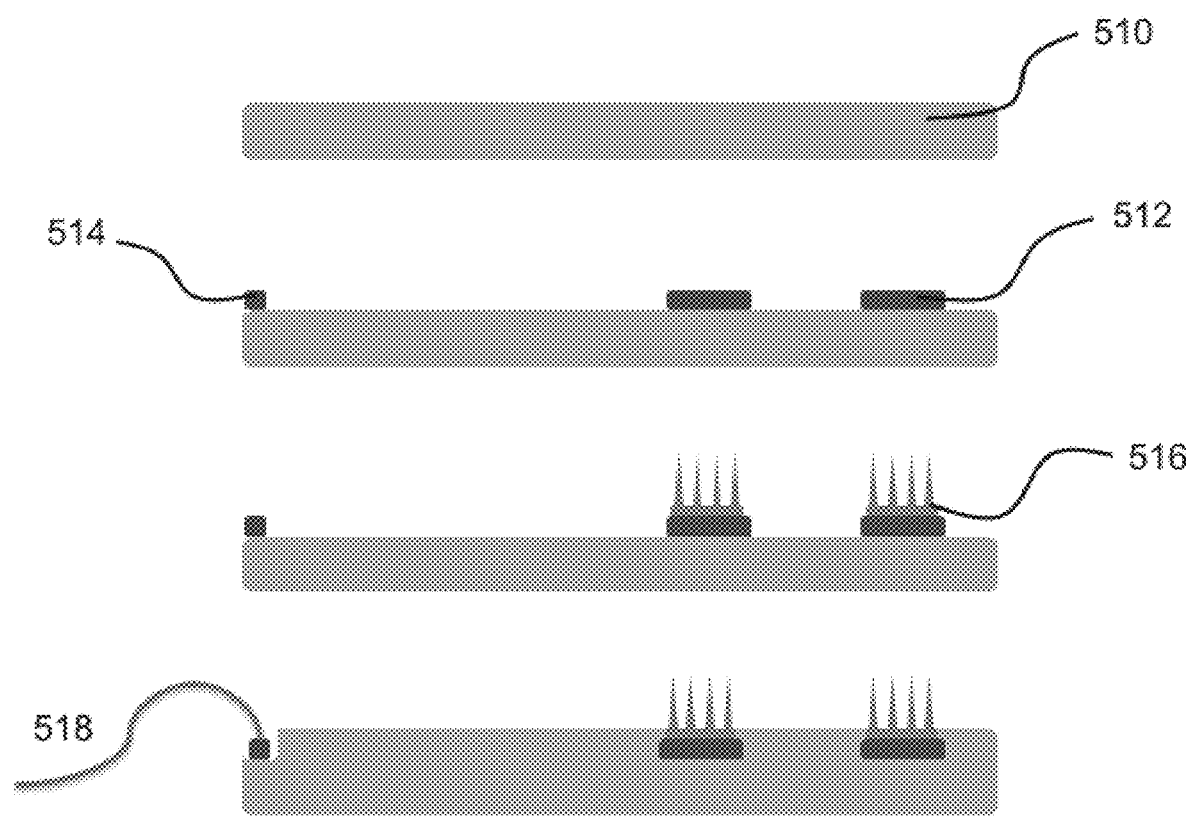
FIG. 5 is an illustration of a potential fabrication method of a neural interfacing device.

FIG. 5 illustrates one example method of fabrication a microneedle electrode. In this embodiment, the first step involves forming a first layer of Kapton 510. Next, metal pads 512 are defined on the Kapton 510 substrate using, for example, established microfabrication processes such as thin film deposit/etch, thin film lift-off, screen printing, electroplating, electroless plating, shadow masking of thin film metal, and the like. Metal pads 512 may include additional components for interacting with microneedle electrodes. For example, they may include traces for electrical connections. Additionally, electrical connector 514 is attached to the Kapton 512 layer to support a wire 518 connecting to, for example, external electronics. Electrical connector 514 may take the form of any component capable of electrical communication, including wireless transmission. In this embodiment, the next step is placing microneedle electrodes 516 onto the metal pads 512. Finally, a second layer of Kapton 510 is added. In some embodiments, the second layer of Kapton 510 covers at least a portion of the metal pads 512 and/or the microneedle electrodes 516. This particular method of fabrication is merely one example; a person of ordinary skill would understand that any other suitable fabrication techniques may be utilized.

In another aspect, the microneedle arrays can be formed monolithically on the substrate by using polymer micromachining and micro-molding technologies. In this implementation, the substrate can be a flexible or standard polymer such as, for example and without limitation, PDMS, thin Kapton, thin polyimide, thin polyetheylene naphthalate, SU-8, PMMA (poly methyl methacrylate), COC (cyclic olefin copolymer), PLGA (polylactic-co-glycolic acid), PLA (polylactic acid), or other suitable substitutes. Further, it is contemplated that the packaging can comprise, for example and without limitation, flex circuit interfacing with the microneedle electrode through mechanical fusion or using conductive PDMS or conductive epoxies as an intermediate material.

The microneedles may be manufactured from various materials, including at least one of stainless steel, platinum, platinum/iridium, palladium, silver, silver chloride, titanium nitride, titanium, iridium, iridium oxide, iridium tin oxide, PEDOT, carbon nanotubes, epoxies, polymers, and conductive polymers. Further, it is contemplated that the packaging can comprise, for example and without limitation, flex circuit interfacing with the microneedle electrode through mechanical fusion or using conductive PDMS or conductive epoxies as an intermediate material.

Figure 6:
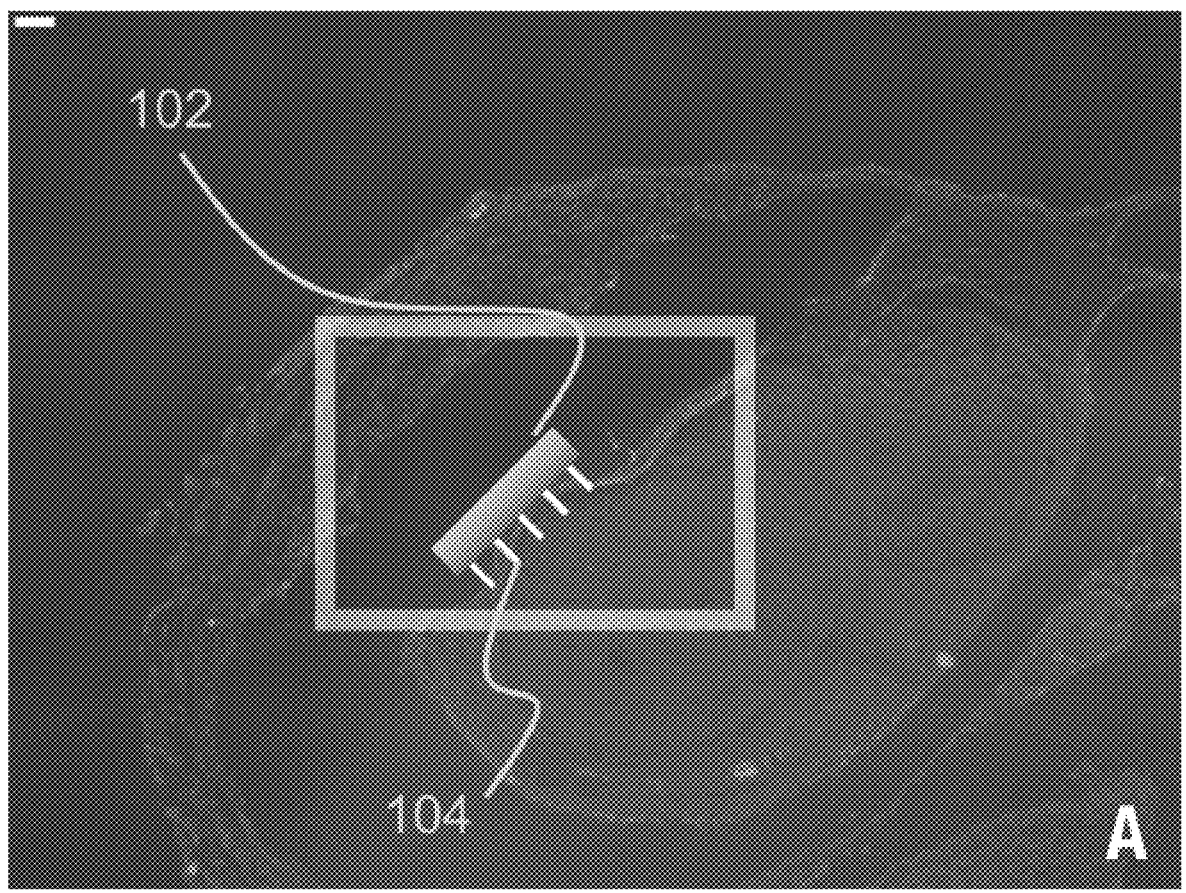
FIG. 6 is a radial cross section of a sciatic nerve with a microneedle electrode implanted.

FIG. 6 shows a radial cross section of a sciatic nerve with a microneedle electrode 102 implanted. From this angle, five microneedles 104 of the microneedle electrode 102 are visible. All of the visible microneedles 104 appear to have penetrated at least a portion of the epineurium layer of the nerve. Some of those microneedles 104 also appear to have penetrated the axon area of the nerve, but only minimally. In some embodiments, this penetration is less than 500 micrometers. As explained above, in different embodiments the microneedles 104 may not penetrate the axon area at all, or may penetrate any distance from between about 0 to about 500 micrometers.

Figure 7:
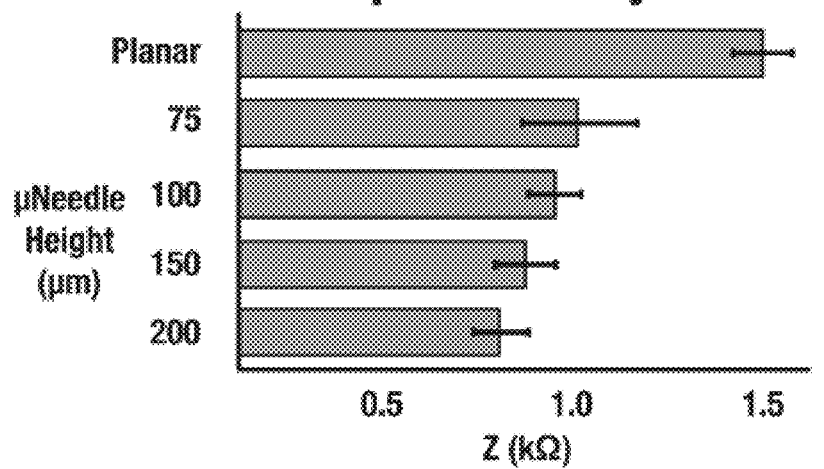
FIG. 7 shows three charts comparing the electrical performance of microneedle electrodes to conventional electrodes in an in-vivo setting.
Figure 7:
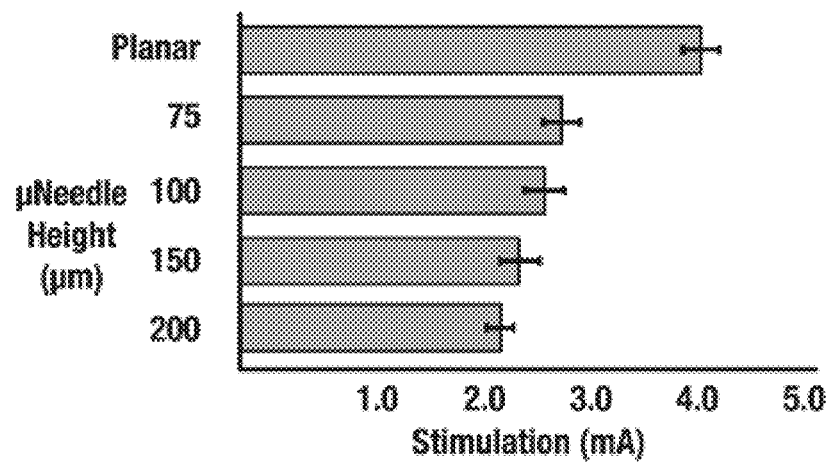
Figure 7:
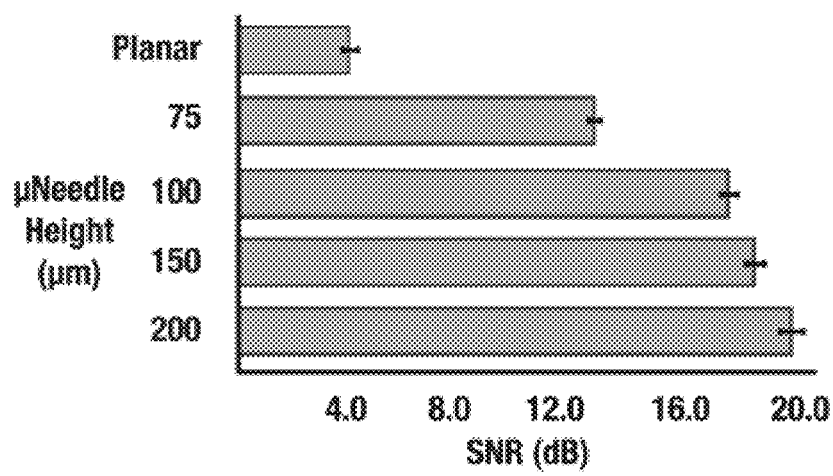

FIG. 7 highlights the advantages of using microneedles 104 as disclosed herein, especially with respect to using a planar electrode that merely interfaces with the outer surface of a nerve. As shown in the charts of FIG. 7, nerve-electrode impedance decreases as needle height increases up to, for example, 200 micrometers. Similarly, stimulation threshold decreases up to 200 micrometers. Finally, the signal-to-noise ratio increases up to 200 micrometers. In one aspect, the microneedle surface configuration can lower the amount of current required for stimulation compared to conventional electrodes, thereby increasing safety and increasing the lifetime of the microneedle electrodes when used in chronic settings. In another aspect, the microneedle surface configuration can increase the signal-to-noise ratio of nerve recordings over conventional electrodes. These advantages may lead to longer battery life of implantable devices. Additionally, lower current requirements may prevent nerve damage over time. Finally, lower currents may also lead to longer electrode life due to less degradation of electrical characteristics.

Figure 8:
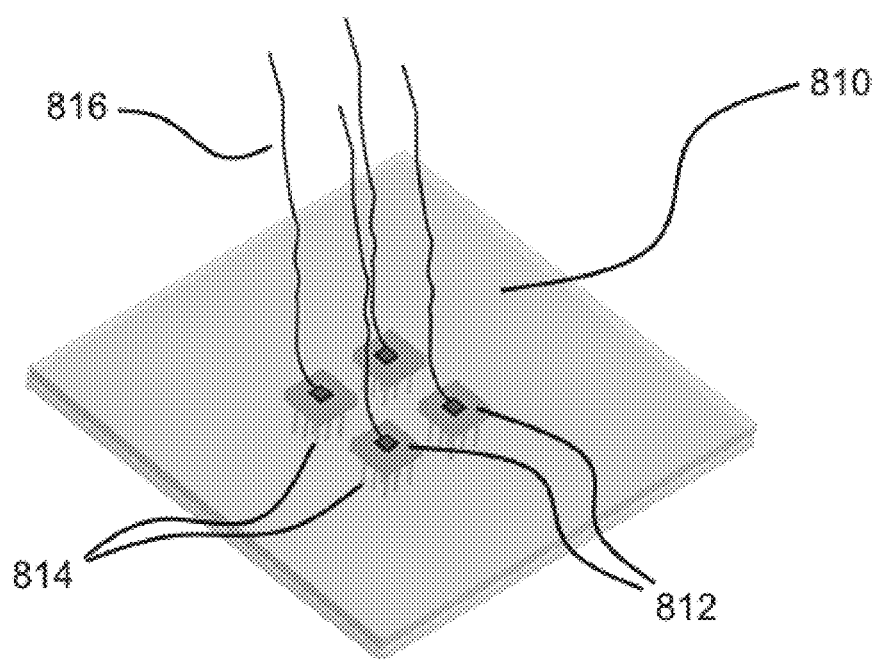
FIG. 8 is a perspective view of a schematic showing a neural interfacing device having a 2×2 array of microneedle electrodes attached to a planar assembly.

FIG. 8 shows an embodiment of a neural interfacing device having a 2×2 array of microneedle electrodes 812 attached to a planar assembly 810. As discussed above, a planar assembly 810 may be employed instead of, or in addition to, a cuff assembly. Other shapes and sizes of assemblies are contemplated. However, a planar assembly may be more suitable for applying microneedle electrodes 812 to bundles of nerves that may otherwise be difficult to access with a cuff assembly. The embodiment shown in FIG. 8 illustrates the microneedle electrodes 812 having microneedles 814 as well as wires 816 leading to, for example, external electronics.

Figure 9:
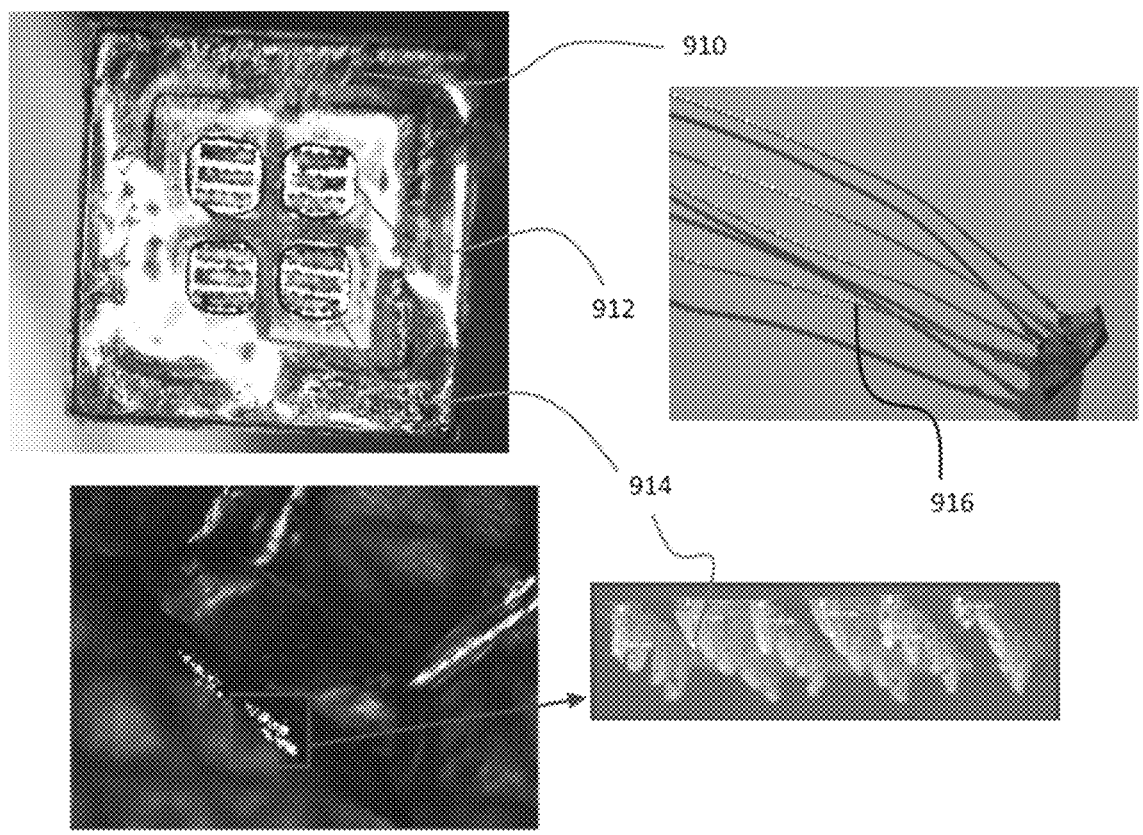
FIG. 9 shows examples of commercial embodiments of planar neural interfacing assemblies.

FIG. 9 shows examples of commercial embodiments of neural interfacing devices. For example, the figure shows a neural interfacing device having a 2×2 array of microneedle electrodes 912 attached to a planar assembly 910. FIG. 9 also shows an array of microneedles 914 protruding from the microneedle electrodes 912 in a three-dimensional fashion. A plurality of wires 916 are also shown protruding from a microneedle electrode. Other wire configurations, including having different numbers of wires, are also contemplated.

It is also contemplated that the microneedle surface can increase the mechanical stability of the electrode assembly and therefore the performance of the system by reducing or eliminating any relative movement between the at least one microneedle electrode and target nerve. For example, the penetration of microneedles into the epineurium may serve to act as an anchor for the neural interfacing device. In one embodiment, the anchoring effect of the microneedles causes the microneedle electrode to remain in one position on the nerve. This, in turn, provides the entire neural interfacing device with additional stability relative to the nerve. For example, the neural interfacing device is less likely to slide along a nerve or rotate about the nerve when the microneedles have penetrated the epineurium of the target nerve or bundle of nerves. Additionally, anchoring may help to maintain sufficient contact between the microneedle electrodes and the nerve, thus lowering the current requirements for stimulation.

In one operational aspect, after a target nerve is exposed, the neural interfacing device can be applied where the at least one microneedle electrode is in contact with a target location on the nerve, the cuff can be connected to stimulation electronics, and the stimulation electronics can cause stimulation of the nerve via the microneedle electrodes. During and immediately after stimulation, data can be collected from a point downstream from the target location either on the nerve or an associated muscle in order to establish the stimulation threshold required for maximum stimulation. Also, with the same configuration, a stimulus could be applied to a location on the nerve downstream from the target location and the response of the nerve recorded at the target location via the microneedle electrode in order to establish a signal-to-noise ratio. It is contemplated that the neural interfacing device can have a wired configuration where the microneedle electrode assembly and stimulation electronics are connected via wires.

In one embodiment, the neural interfacing device comprises at least one microneedle having a height of from about 10 micrometers to about 10 millimeters. In another aspect, the at least one microneedle can have a sharpness from about 0.1 to about 100 micrometers. In yet another aspect, the microneedle electrode can have a pitch separating it from the neighboring electrode of from about 100 micrometers to about 100 millimeters. The thickness of the material comprising the microneedles can be at least about 10 micrometers to about 2 millimeters. In another aspect, the microneedle electrode can have from one microneedle to about 1000 microneedles forming an array. More preferably, the microneedle electrode has from about two microneedles per array to about 100 microneedles per array.

In one embodiment, the neural interfacing device may include an electrical shielding layer on an outer surface of the device. For example, if the neural interfacing device includes an elongate cuff, the elongate cuff may have an electrical shielding layer on its outer surface. In some embodiments the electrical shielding layer functions to shield the electronic components from electrical noise, thereby strengthening the signals sent to and from the microneedle electrodes.

In a further or additional aspect, the nerve interfacing device of the present invention could be used to regenerate severed or otherwise damaged nerves. Here, it is contemplated that the microneedle surface can serve to bind a severed or damaged nerve, and the external stimulation of the nerve via the microneedle electrode can facilitate nerve repair or regeneration.

Accordingly, FIGS. 1-7 and the corresponding text provide a number of different components and mechanisms for electrical stimulation of or recording activity of nerves. In addition to the foregoing, implementations described herein can also be described in terms acts and steps in a method for accomplishing a particular result. For example, a method comprising at least one of exposing a nerve, placing at least one microneedle electrode comprising a microneedle array in contact with a target location on the nerve, securing the at least one microneedle electrode about the nerve, placing the microneedle electrode in communication with stimulating electronics, stimulating the nerve and recording the electrical activity of the nerve is described concurrently above with reference to the components and diagrams of FIGS. 1-7.

The present invention can thus be embodied in other specific forms without departing from its spirit or essential characteristics. The described aspects are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A neural interfacing device, comprising:
a microneedle electrode comprising a conductive body that comprises a plurality of microneedles, wherein the conductive body has a void formed therein, wherein the void surrounds the plurality of microneedles, wherein the plurality of microneedles are bent outward with respect to the conductive body to form a three-dimensional microneedle electrode, and wherein each of the plurality of microneedles is sized and shaped to penetrate a nerve epineurium.

2. The neural interfacing device of claim 1, further comprising:
a planar base comprising an inner surface and an outer surface; and
wherein the microneedle electrode is fixed to the inner surface of the planar base.

3. The neural interfacing device of claim 1, further comprising:
an elongate cuff comprising an outer surface and an inner surface and sized to fit at least partially around a nerve;
wherein the microneedle electrode is fixed to the inner surface of the elongate cuff; and
wherein the elongate cuff is configured to fit to the nerve.

4. The neural interfacing device of claim 1, wherein each of the plurality of microneedles is sized and shaped to penetrate the nerve epineurium without any portion of the microneedle electrode penetrating any nerve axon beyond a depth of 500 micrometers.

5. The neural interfacing device of claim 1, wherein each of the plurality of microneedles is sized and shaped to penetrate the nerve epineurium without any portion of the microneedle electrode penetrating any nerve axon.

6. The neural interfacing device of claim 1, wherein when the microneedle electrode is applied to a nerve or bundle of nerves, the plurality of microneedles anchor the neural interfacing device with respect to the nerve or bundle of nerves.

7. The neural interfacing device of claim 6, wherein the plurality of microneedles provide stability to the neural interfacing device such that it remains in position with respect to the nerve or bundle of nerves.

8. The neural interfacing device of claim 1, wherein each of the plurality of microneedles has a height of about 10 micrometers to about 10 millimeters.

9. The neural interfacing device of claim 1, wherein the conductive body is a metal pad.

10. The neural interfacing device of claim 1, wherein the plurality of microneedles comprise between 2 and 1000 microneedles.

11. The neural interfacing device of claim 1, wherein the neural interfacing device comprises at least two microneedle electrodes, wherein one of the at least two microneedle electrodes is the microneedle electrode.

12. The neural interfacing device of claim 1, wherein the neural interfacing device comprises at least three microneedle electrodes, wherein one of the at least three microneedle electrodes is the microneedle electrode.

13. The neural interfacing device of claim 1, wherein the neural interfacing device comprises an array of microneedle electrodes, wherein the array of microneedle electrodes includes the microneedle electrode.

14. The neural interfacing device of claim 13, wherein the array of microneedle electrodes is a grid pattern having from 4 to 1000 microneedle electrodes.

15. The neural interfacing device of claim 1, wherein the neural interfacing device is connected to stimulation electronics via electrical connectors.

16. The neural interfacing device of claim 1, wherein the microneedle electrode is a single electrode.

17. The neural interfacing device of claim 1, wherein the microneedle electrode is configured as a single channel for applying stimulus or receiving data.

18. The neural interfacing device of claim 1, wherein the microneedle electrode is configured to monitor electrical signals within a nerve.

19. The neural interfacing device of claim 1, wherein the microneedle electrode is configured to apply an electrical stimulus to a nerve.

\* \* \* \* \*